(12) United States Patent
Landis et al.

(10) Patent No.: US 7,189,883 B2
(45) Date of Patent: Mar. 13, 2007

(54) DIAZAPHOSPHOLANE LIGANDS FOR ASYMMETRIC CATALYSIS

(76) Inventors: Clark Landis, 1852 Summit Ave., Madison, WI (US) 53705; Thomas P. Clark, 58 Atherton St. #1R, Somerville, MA (US) 02143; Jerzy Klosin, 2209 Parkwood Dr., Midland, MI (US) 48642

( * ) Notice: Subject to any disclaimer, the term of this patent is extended or adjusted under 35 U.S.C. 154(b) by 0 days.

(21) Appl. No.: 11/211,918

(22) Filed: Aug. 25, 2005

(65) Prior Publication Data

US 2006/0069281 A1    Mar. 30, 2006

Related U.S. Application Data

(60) Provisional application No. 60/605,153, filed on Aug. 27, 2004.

(51) Int. Cl.
C07C 45/50    (2006.01)
C07C 253/00   (2006.01)
C07C 67/00    (2006.01)

(52) U.S. Cl. .................. 568/454; 558/332; 560/241

(58) Field of Classification Search .................. None
See application file for complete search history.

(56) References Cited

U.S. PATENT DOCUMENTS

| | | | |
|---|---|---|---|
| 5,491,266 | A | 2/1996 | Babin et al. |
| 5,530,150 | A | 6/1996 | Takaya et al. |
| 2003/0040629 | A1 | 2/2003 | Zhang |
| 2003/0055254 | A1 | 3/2003 | Landis et al. |
| 2003/0144137 | A1 | 7/2003 | Zhang et al. |
| 2003/0171608 | A1 | 9/2003 | Reetz et al. |
| 2004/0072680 | A1 | 4/2004 | Zhang |
| 2004/0199023 | A1 | 10/2004 | Whiteker et al. |
| 2004/0229846 | A1 | 11/2004 | Zhang et al. |

FOREIGN PATENT DOCUMENTS

| | | |
|---|---|---|
| WO | WO 03/010174 | 2/2003 |
| WO | WO 03/042135 | 5/2003 |

OTHER PUBLICATIONS

Breeden, et al., "Rhodium-Mediated Asymmetric Hydroformylation with a Novel Bis(diazaphospholidine) Ligand", Angew. Chem. Int. Ed., vol. 39, No. 2, 2000, pp. 4106-4108

Clark et al., "Resolve Chiral 3,4-Diazaphospholanes and Their Application to Catalytic Asymmetric Allylic Alkylation", J. Amer. Chem. Soc., vol. 125, 2003, pp. 11792-11793.
Clark et al., "A 1,2,4-diazaphospolane complex of rhodium," Acta Crystallographica Section C, vol. C59, 2003, m144-m145.
Cobley, et al., "Synthesis and Application of a New Bisphosphite Ligand Collection for Asymmetric Hydroformylation of Allyl Cyanide", J. Org. Chem., vol. 69, 2004, pp. 4031-4040.
Kwok et al., "Characterization and Application of Catalytic Regioselective Hydroformylation with a Cationic Bis(dioxaphospholane)rhodium Catalyst Precursor," Organometallics, vol. 12, 1993, pp. 1954-1959.
Lambers-Verstappen, et al., "Rodium-Catalysed Asymmetric Hydroformylation of Unsaturated Nitriles", Adv. Synth. Catal., 2003, vol. 345, No. 4, pp. 478-482.
Landis, et al., "Rapid Access to Diverse Arrays of Chiral 3,4-Diazaphospholanes", Angew. Chem. Int. Ed., vol. 40, No. 18, 2001, pp. 3432-3434.
Landis, et al., "Solid-phase synthesis of chiral 3,4-diazaphospholanes and their application to catalytic asymmetrix allylic alkylation", Proceedings of the National Acadmy of Sciences of the United States, vol. 101, 2004, pp. 5428-5432.
Nozaki et al., "Highly Enantioselective Hydroformylation of Olefins Catalyzed by Rhodium(I) Complexes of New Chiral Phosphine-Phosphite Ligands," J. Am. Chem. Soc., vol. 119, 1997, pp. 4413-4423.
Sakai et al., "Highly Enantioselective Hydroformylation of Olefins Catalyzed by New Phosphinephosphite-Rh(I) Complexes", J. Am. Chem. Soc., vol. 115, 1993, pp. 7033-7034.
Stille et al., "Platinum-Catalyzed Asymmetric Hydroformylation of Olefins with (-)-BPPM/SnCl$_2$-Based Catalyst Systems", Organometallics, vol. 10, 1991, pp. 1183-1189.
Cobley, et al., "Parallel Ligand Screening on Olefin Mixtures in Asymmetric Hydroformylation Reactions," Org. Lett., vol. 6, No. 19, pp. 3277-3280 (2004).
van Leeuwen, P.W.N.M. and Claver, C., Rhodium Catalyzed Hydroformylation, Kluwer Academic Publishers, Dordrecht, 2000.
Clark et al., "Highly Active, Regioselective, and Enantioselective Hydroformylation with Rh Catalysts Ligated by Bis-3,4-diazaphospholanes," J. Am. Chem. Soc., vol. 127, pp. 5040-5042 (2005).

Primary Examiner—Sikarl A. Witherspoon

(57) ABSTRACT

This invention relates to asymmetric hydroformylation processes in which a prochiral or chiral olefin is reacted with carbon monoxide and hydrogen in the presence of an optically active metal-ligand complex catalyst to produce an optically active aldehyde or a product derived from an optically active aldehyde.

32 Claims, 1 Drawing Sheet

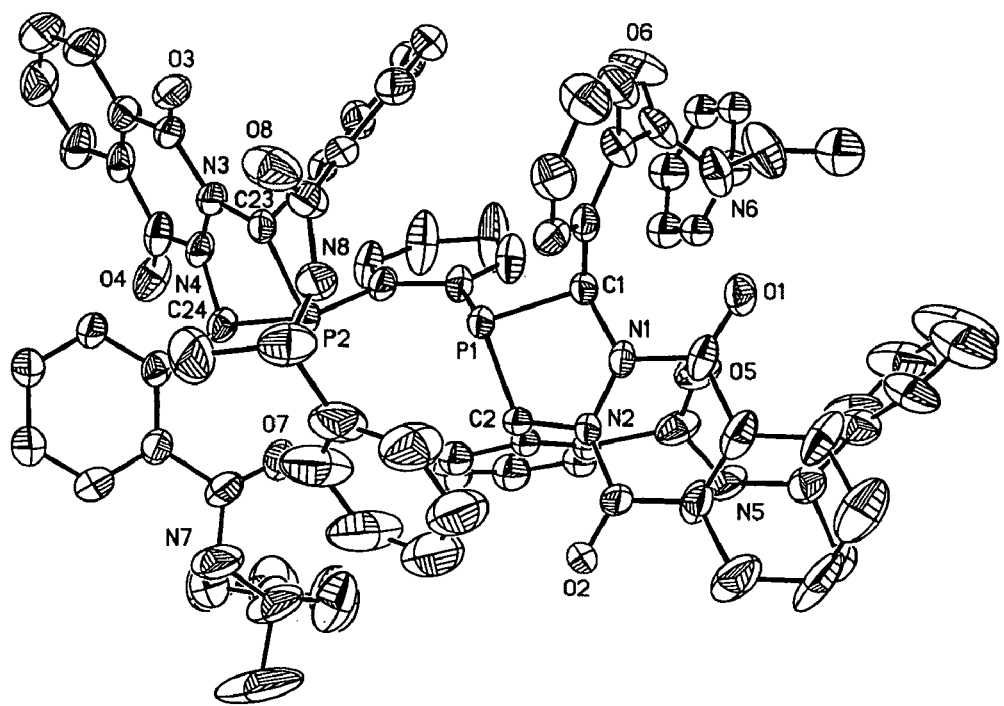
Figure 1. Molecular structure and labeling scheme for TPC-486-2 ligand with 40% probability of thermal ellipsoids. Hydrogen atoms are removed for clarity.

DIAZAPHOSPHOLANE LIGANDS FOR ASYMMETRIC CATALYSIS

This application claims the benefit of U.S. Provisional Application No. 60/605,153, filed Aug. 27, 2004.

FIELD OF THE INVENTION

This invention relates to asymmetric hydroformylation processes in which a prochiral or chiral olefin is reacted with carbon monoxide and hydrogen in the presence of an optically active metal-ligand complex catalyst to produce an optically active aldehyde or a product derived from an optically active aldehyde.

BACKGROUND TO THE INVENTION

Asymmetric synthesis is of importance, for example, in the pharmaceutical industry, since frequently only one optically active isomer (enantiomer) is therapeutically active. An example of such a pharmaceutical product is the non-steroidal anti-inflammatory drug Naproxen. The (S)-enantiomer is a potent anti-arthritic agent while the (R)-enantiomer is a liver toxin. It is therefore often desirable to selectively produce one particular enantiomer over its mirror image.

It is known that special precautions must be taken to ensure production of a desired enantiomer because of the tendency to produce optically inactive racemic mixtures; that is, equal amounts of each mirror image enantiomer whose opposite optical activities cancel out each other. In order to obtain the desired enantiomer or mirror image stereoisomer from such a racemic mixture, the racemic mixture must be separated into its optically active components. This separation, known as optical resolution, may be carried out by actual physical sorting, direct crystallization of the racemic mixture, or other methods known in the art. Such optical resolution procedures are often laborious and expensive and normally the yield of the desired enantiomer is less than 50% based on the racemic mixture feedstock. Due to these difficulties, increased attention has been placed upon asymmetric synthesis in which one of the enantiomers is obtained in significantly greater amounts. In particular, asymmetric synthesis processes facilitated by catalysis with transition metal complexes of single enantiomer chiral ligands (asymmetric catalysis) is finding ever increasing industrial applicability for pharmaceuticals and in other sectors.

Asymmetric hydroformylation of olefins is especially valuable for the synthesis of optically active products, since the reaction is a one-carbon homologation that also establishes a chiral center. Efficient asymmetric hydroformylation desirably affords the ability to control both regioselectivity (branched/linear ratio) and enantioselectivity. The optically active aldehyde that is produced in asymmetric hydroformylation can be further elaborated into other functional groups, either by subsequent reaction steps or via in situ reaction with other reagents.

Various asymmetric hydroformylation catalysts have been described in the art, see van Leeuwen, P. W. N. M. and Clayer, C., "Rhodium Catalyzed Hydroformylation", Kluwer Academic Publishers, Dordrecht, 2000. For example, Stille, John K. et al., Organometallics 1991, 10, 1183–1189 relates to the synthesis of three complexes of platinum(II) containing the chiral ligands 1-(tert-butoxycarbonyl)-(2S,4S)-2-[(diphenylphosphino)methyl]-4-(dibenzophospholyl)pyrrolidine, 1-(tert-butoxycarbonyl)-(2S,4S)-2-[(dibenzophospholyl)methyl]-4-(diphenylphosphino)pyrrolidine and 1-(tert-butoxycarbonyl)-(2S,4S)-4-(dibenzophospholyl)-2-[(dibenzophospholyl)methyl]pyrrolidine. Asymmetric hydroformylation of styrene was examined with use of platinum complexes of these three ligands in the presence of stannous chloride as catalyst. Various branched/linear ratios (0.5–3.2) and enantiomeric excess values (12–77%) were obtained. When the reactions were carried out in the presence of triethyl orthoformate, all four catalysts gave virtually complete enantioselectivity (ee >96%) and similar branched/linear ratios. However, platinum hydroformylation catalysts are of limited utility due to their low catalytic activity and requirement for high $CO/H_2$, i.e. syn gas, pressures.

Takaya, H., et al, J. Am. Chem. Soc. 1993, 115, 7033 reported the use of the mixed phosphine-phosphite ligand, BINAPHOS, for use in rhodium catalyzed hydroformylation. Enantioselectivities as high as 96% were observed for styrene hydroformylation, although the regioselectivity (branched/linear) was relatively low. Lambers-Verstappen, M. M. H. and de Vries. J. G, Adv. Synth. Catal., 2003, 345, 478–482 report application of BINAPHOS for the Rh-catalyzed hydroformylation of allyl cyanide; this process was only moderately selective, giving chiral aldehyde product of 66% ee and a branched/linear ratio of 72:28. Wills, M. and coworkers reported (Angew. Chem. Int. Ed., 2000, 39, 4106) the use of chiral diazaphospholidine ligand, ESPHOS, for Rh-catalyzed asymmetric hydroformylation of vinyl acetate. Enantioselectivities up to 92% ee were obtained for vinyl acetate. This ligand, however, was ineffective in the hydroformylation of styrene, giving a racemic mixture.

U.S. Pat. No. 5,491,266 to Union Carbide discloses highly effective chiral bisphosphite ligands for use in Rh-catalyzed asymmetric hydroformylation. Ligands prepared from optically active diols which bridge two phosphorus atoms were especially useful for a variety of olefin substrates. Preferred ligands, for example the prototype ligand known as Chiraphite, were prepared from optically active (2R,4R)-pentanediol and substituted biphenols. The highest regioselectivities and enantioselectivities (>85% ee) were observed with vinylarene substrates. Other substrates were hydroformylated with lesser selectivities.

Recently, a new type of ligand family was introduced where two optically active phosphite moieties are linked by achiral bridges (Cobley, C. J. et al., J. Org. Chem., 2004, 69, 4031 and Org. Lett., 2004, in press). The best ligand identified, Kelliphite, was shown to be enantio- and regioselective for the asymmetric hydroformylation of allyl cyanide (78% ee, b/l=18, at=35° C.) and vinyl acetate (88% ee, b/l=125, at=35° C.).

Despite the advances made in asymmetric hydroformylation technology as described above, existing ligands are limited in scope and predictability of performance. Accordingly, there is a need for wider range of chiral ligands for catalytic asymmetric hydroformylation, especially for multipurpose ligands showing improved activity and selectivity profile, conferring favourable process economics across a range of substrates. Such substrates include, without limitation, styrene and other vinyl arenes, vinyl acetate and allyl cyanide. Another desired feature is that the ligand structure has modular design which can be systematically varied to obtain the best results for any given olefinic substrate. Lastly, for commercial applications, it is a requirement for favorable process economics that the chosen ligand for an asymmetric hydroformylation process can be synthesized efficiently from readily available raw materials. In seeking to design improved ligands, in general the known art teaches need for phosphite-containing or other hetero-phosphine ligands to achieve the level of activity required for rhodium-catalyzed hydroformylation, whereas diphosphine ligands (i.e. containing 2 phosphine group, in each of which the P atom bears three optionally substituted hydrocarbon substituents), often associated with asymmetric hydrogenation applications, are usually considered to less effective. Indeed, van Leeuwen and Clayer, idem, p. 131, have noted that "despite all the efforts made to apply diphosphines in asymmetric hydroformylation, the enantioselectivities of rhodium-diphosphine systems are not has high as those of rhodium-diphosphite or rhodium phosphine-phosphite systems."

Landis, C. R. and coworkers have recently disclosed (PCT application 03/010174; Angew. Chem. Int. Ed. 2001, 40, 3432) the preparation of novel mono and diphosphines based on the 3,4-diazaphospholane ring structure as shown below. In specific examples of diphosphines reported to date, the substituent $R^2$ is unsubstituted phenyl. In specific examples of monophosphines reported to date, the substituent $R^2$ can be alkyl, unsubstituted aryl (e.g. phenyl, 2-naphthyl), unsubstituted heteroaryl (e.g. 2-furanyl), o-tolyl, or phenyl group substituted with OH, OAc, F, carboxyl or carboxamide groups.

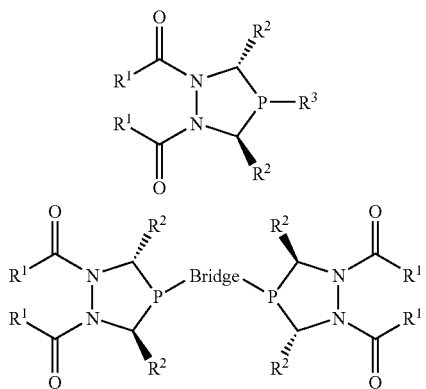

These phosphines were shown to be easily synthesized from readily available materials and can be easily modified to alter their electronic and steric characteristics. Transition metal complexes of such phosphines have been shown to have utility as catalysts for asymmetric allylic alkylation (palladium complexes) and asymmetric hydrogenation (rhodium complexes). Monodentate phosphines were applied, for example, as ligands in allylic alkylation reactions (Clark, T. P.; Landis, C. R. J. Am. Chem. Soc. 2003, 125, 11792. Landis, C. R; Clark, T. C, Proceedings of the National Academy of Science 2004, 101, 5428–5432).

SUMMARY OF THE INVENTION

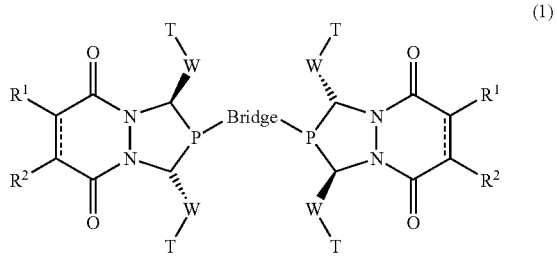

(1)

The present invention is based on the discovery of synthetically useful processes in which an olefin undergoes an asymmetric reaction selected from the group consisting of hydroformylation, hydrocyanation, hydrocarboxylation and hydroesterification, in the presence of, as catalyst, a transition metal complex of a bis(diazaphospholane) ligand according to formula (1), or the opposite enantiomer thereof, wherein (a) Bridge is a linking group selected from the group consisting of substituted and unsubstituted alkyl, substituted and unsubstituted alkenyl, substituted and unsubstituted aryl, substituted and unsubstituted heterocyclyl, and substituted and unsubstituted ferrocenyl groups; (b) W, at each occurrence, is independently selected from the group consisting of substituted and unsubstituted aryl and heteroaryl, substituted and unsubstituted cycloalkyl, substituted and unsubstituted heterocyclyl, and substituted and unsubstituted alkyl; (c) T, at each occurrence, is independently selected from the group consisting of —C(O)OR$^3$, —C(O)NR$^4$R$^5$, —C(O)N(R$^4$)OR$^5$, OR$^3$, NR$^4$R$^5$, substituted and unsubstituted oxazole, substituted and unsubstituted oxazoline, substituted and unsubstituted oxazolidine, and substituted and unsubstituted alkyl; (d) R$^1$ and R$^2$ are independently selected from the group consisting of H, substituted and unsubstituted alkyl, substituted and unsubstituted cycloalkyl, and substituted and unsubstituted aryl; or R$^1$ and R$^2$ may join together to form a substituted or unsubstituted aryl, a substituted or unsubstituted cycloalkyl, or a substituted or unsubstituted cycloalkenyl; (e) R$^3$, R$^4$ and R$^5$ are each independently selected from the group consisting of —H, substituted and unsubstituted alkyl, substituted and unsubstituted aryl, substituted and unsubstituted aralkyl, substituted and unsubstituted heterocyclyl, substituted and unsubstituted heterocyclylalkyl; or R$^4$ and R$^5$ may join together to form a non-aromatic heterocyclyl; and (f) the dashed line, at each occurrence, represents an optional additional bond, such that a single or double carbon-carbon bond exists between C(R$^1$) and C(R$^2$).

The primary application of the present invention is in hydroformylation reactions. In view of the synthetically useful hydroformylation reactions as detailed below, the utility of the aforementioned transition metal complexes in related reactions of olefins, comprising hydrocyanation, hydrocarboxylation and hydroesterification, will be readily appreciated by those skilled in the art.

BRIEF DESCRIPTION OF THE DRAWING

FIG. 1 is a molecular structure and labeling scheme for TPC-486-2 ligand.

DETAILED DESCRIPTION OF THE INVENTION

In one aspect of the present invention, in the process catalyzed by a transition metal complex of compound according to formula (1), the transition metal is selected from the group consisting of rhodium, ruthenium, iridium, palladium, cobalt, platinum, nickel, iron and osmium. Preferably the transition metal is rhodium. In carrying out such a process, the complex is either pre-formed and isolated prior to use, pre-formed in a solution that is then combined in the reaction vessel with the substrate undergoing reaction, or generated in situ during the reaction. In the case of rhodium complexes, it may be preferred that the complex is pre-formed in a solution that is then combined in the reaction vessel with the substrate undergoing reaction. It will be readily appreciated by those skilled in the art that if desired, recognized methods can be applied to achieve immobilization of the ligand (1) and/or a corresponding transition metal complex for the operation of a process according to the present invention. Landis and Clark, 2004, idem, describes one such method.

In another aspect of the present invention, the preferred asymmetric reaction is either hydroformylation or hydrocyanation. More preferably, the reaction is asymmetric hydroformylation of an olefin and the complex is a rhodium complex. Such asymmetric reactions may either entail enantioselective hydroformylation of a prochiral olefin or diastereoselective hydroformylation of an enantiomerically enriched chiral olefin. In either case, it is desirable that the enantioselective excess of the required product is at least 60% and is preferably at least 80%, or higher. In such hydroformylation reactions the olefin is typically, although not always, a prochiral α-olefin, i.e. a monosubstituted terminal olefin. Hydroformylation of a prochiral α-olefin $RCH=CH_2$ may result in the formation of two regiosiomeric aldehydes, a branched chiral aldehyde $RCH(CHO)CH_3$ and a linear achiral aldehyde $RCH_2CH_2CHO$. In the process of the present invention, it is desirable the branched aldehyde is the major product, such that the ratio of branched:linear aldehyde products is at least 3:1 and is preferably at least 8:1, or higher. The α-olefin may be selected from the group consisting of, but not limited to, styrene, vinyl acetate, and allyl cyanide.

In yet another aspect of the present invention, wherein the process is hydroformylation, the aldehyde product may be subjected to derivatizion. For such purpose, depending on the synthetic application, the derivatizing reaction comprises an oxidation, reduction, amination, olefination, condensation, esterification, alkylation, arylation or acylation reaction.

In yet another aspect of the present invention, in the process catalyzed by a transition metal complex of compound according to formula (1), preferred features of compound (1) can be characterized as follows:

(i) P-Bridge-P in compound (1) is selected from the group comprising formulae (2) to (7), each of which may be optionally substituted; n in (3) is in the range 0–5; X in (6) is either O or N-alkyl. More preferably P-Bridge-P is either (2) or (3) in which n is 1 and most preferably P-Bridge-P is (2). With respect to the backbone structures (2) to (7), it will be readily appreciated by those skilled in the art that substitution of alternative backbone structures may be possible in order to obtain ligands with similar properties in asymmetric synthesis applications;

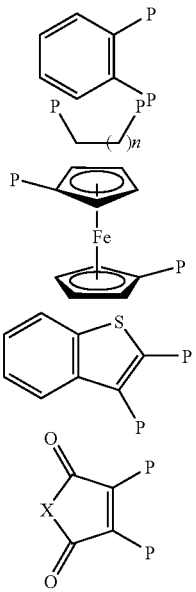

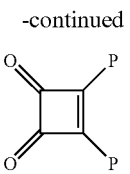

(ii) Every W-T group in compound (1) is identical. More preferably in such ligands W in compound (1) is either substituted or unsubstituted aryl or heteroaryl and each T in W is ortho relative to the position attached to the diazaphospholane ring. Most preferably, W may be 1,2-phenylene;

(iii) T in compound (1) is —C(O)NR$^4$R$^5$. More preferably the group NR$^4$R$^5$ is derived from a chiral amine H—NR$^4$R$^5$ in which typically R$^4$ is H. Most preferably the chiral amine is either a 1-aryl ethylamine or an alkyl ester of an α-amino acid, and may be selected from the group consisting of (R)-1-phenylethylamine, (S)-1-phenylethylamine, (R)-1-(1-naphthylethylamine), (S)-1-(1-naphthylethylamine), methyl and ethyl esters of (S)-alanine, methyl and ethyl esters of (R)-alanine; and (iv) Each diazaphospholane ring in compound (1) is incorporated into a tricycle represented by partial formula (8) or a bicycle represented by partial formula (9).

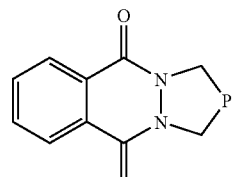

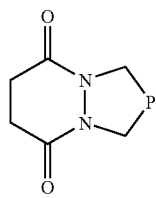

For operation of a process according to present invention, a particularly preferred compound (1) is more specifically represented by formula (10), or the opposite enantiomer thereof.

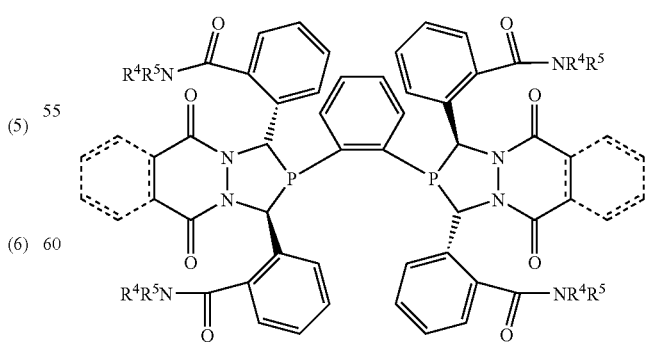

The invention is further illustrated by the Examples below:

Examples 1 and 2 describe the synthesis of tetracarboxylic carboxylic acid variants of (1);

Examples 3–13 describe the synthesis of carboxamide variants of (1), in most cases prepared as a mixture of diastereoisomers which is then separated into constituent diastereoisomers;

Example 14 describes the synthesis of monophosphine counterparts of (1) for use in control experiments within Example 15;

Example 15 describes rhodium-catalyzed hydroformylation reactions of three substrates (styrene, allyl cyanide and vinyl acetate) using ligands of type (1), including direct comparison with monophosphine counterparts of (1) and the known phosphite-based ligands Chiraphite, Kelliphite and Binaphos. Table 1 shows that, unexpectedly for diphosphines, ligands (1) of the present invention are effective for all three substrates, providing good levels of regio- and enantiocontrol, and generally higher activity, as evidenced by % substrate conversion after a fixed time. Table 2 shows the effect of varying reaction temperature and pressure with one particular ligand of type (1); in the case of vinyl acetate in particular, enantioselectivity remains remarkably constant over a broad temperature range;

Example 16 describes X-ray characterization of a ligand of type (1).

General Considerations. All syntheses were carried out under nitrogen using standard Schlenk techniques. Flash chromatography of the amides was done open to air. THF was distilled over Na/benzophenone. Phthaloyl dichloride was purified by vacuum distillation. 1,2-bis(phosphino)benzene was purchased from Strem. All other chemicals were purchased from Aldrich. In the following examples, where applicable the structure of each product is shown before the corresponding experimental description.

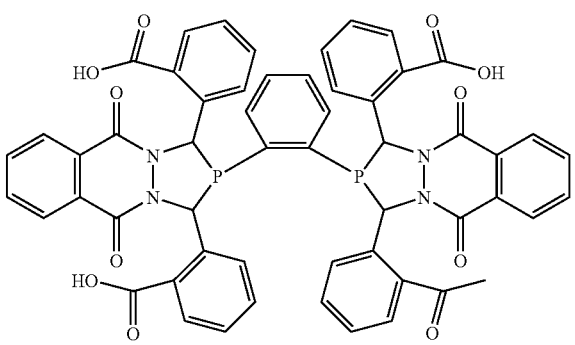

EXAMPLE 1

Synthesis of rel-2,2',2'',2'''-(1,2-phenylenebis((1R,3R)-5,10-dihydro-5,10-dioxo-1H-(1,2,4)diazaphospholo(1,2-b)phthalazine-2,1,3(3H)-triyl))tetrakis-benzoic acid. 2,2'-(Azinodimethylidyne)bis-benzoic acid (1.38 g, 4.66 mmol) was suspended in 80 mL THF at 0° C. 1,2-Bis(phosphino)benzene (0.30 mL, 2.32 mmol) was added to the stirring slurry followed by phthaloyl dichloride (1.00 mL, 6.94 mmol). The reaction was stirred at 0° C. for 1 hour before it was removed from the ice bath and stirred overnight at room temperature. After stirring for 22 hours, the white solid was filtered and rinsed with 20 mL THF. The product was dried under vacuum. Yield=21% of a white solid. $^1$H NMR (d-DMSO): δ 6.25 (d, 2H, J=7.4 Hz), 6.77 (t, 2H J=7.6 Hz), 6.93 (t, 2H, J=7.7 Hz), 7.11 (d, 2H, J=7.8 Hz), 7.29 (broad, 4H), 7.4–7.5 (m, 4H), 7.57 (t, 2H, J=7.6 Hz), 7.68 (s, 2H), 7.74 (t, 2H, J=8.3 Hz), 7.85 (m, 4H, phthaloyl), 7.97 (m, 2H, phthaloyl), 8.05 (d, 2H, J=7.4 Hz), 8.11 (m, 2H, phthaloyl), 12.6 (broad, 4H, COOH); $^{13}$C NMR (d-DMSO): 57.0 (s, PCHN), 60.6 (t, $J_{C-P}$=20 Hz, PCHN), peaks at 125–145 ppm were not assigned, 154.9 (s, CO), 155.2 (s, CO), 167.3 (s, CO), 167.5 (s, CO); $^{31}$P NMR (d-DMSO): 67 –7.9 (broad). EMM calcd for $C_{54}H_{35}N_4O_{12}P_2$ [M–H]$^-$: 993.1727. found: 993.1751.

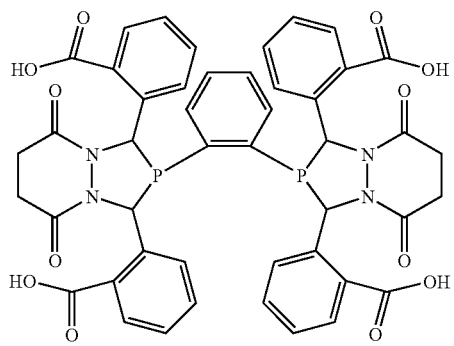

EXAMPLE 2

Synthesis of rel-2,2',2'',2'''-(1,2-phenylenebis((1R,3R)-tetrahydro-5,8-dioxo-1H-(1,2,4)diazaphospholo(1,2-a)pyridazine-2,1,3(3H)-triyl))tetrakis-benzoic acid. 2,2'-(Azinodimethylidyne)bis-benzoic acid (0.92 g, 3.10 mmol) was suspended in 75 mL THF. Bis(phosphino)benzene (0.20 mL, 1.55 mmol) was added to the stirring slurry followed by succinyl dichloride (0.51 mL, 4.63 mmol). After stirring for 20 hours, the solid was filtered by cannula and rinsed with 20 mL THF. The product was dried under vacuum. Yield=33% of a white solid. $^1$H NMR (d-DMSO): δ 2.2–2.5 (m, 6H, CH$_2$CH$_2$), 2.75–2.95 (m, 2H, CH$_2$CH$_2$), 6.49 (m, 2H), 6.82–6.92 (m, 4H), 7.0–7.3 (m, 10H), 7.40 (m, 2H), 7.47 (t, 2H, J=7.5 Hz), 7.63 (t, 2H, J=7.6 Hz), 8.01 (d, 2H, J=8.0 Hz), 12.5 (broad, 4H, COOH); $^{13}$C NMR (d-DMSO): δ 25.4 (s, CH$_2$), 50.7 (broad, PCHN), 54.0 (t, $J_{C-P}$=20 Hz, PCHN), peaks at 120–140 ppm were not assigned, 161.1 (s, CO), 163.3 (s, CO), 163.5 (s, CO), 163.9 (s, CO); $^{31}$P NMR (d-DMSO): δ 5.9 (broad).

General Procedure for Amide Synthesis

The tetracarboxylic acid diazaphospholane (0.34 mmol) was combined with 5 equivalents of PyBOP and placed under nitrogen. Degassed methylene chloride (100 mL) was added followed by 5 equivalents of N,N-diisopropylethylamine and 5 equivalents of the amine [(αS)-α-methylbenzenemethanamine or (αS)-α-methyl-1-naphthalenemethanamine or methyl ester of L-alanine]. After stirring overnight, the solution was opened to the atmosphere and washed with 50 mL each of saturated NaHCO$_3$, 2M HCl, saturated NaHCO$_3$ and H$_2$O. The organic layer was dried over MgSO$_4$, filtered, and the solvent was removed in vacuo. The product was purified by flash chromatography. Full separation of diastereoisomers was accomplished by LC with a Zorbax Rx-Sil column (4.6×250 mm).

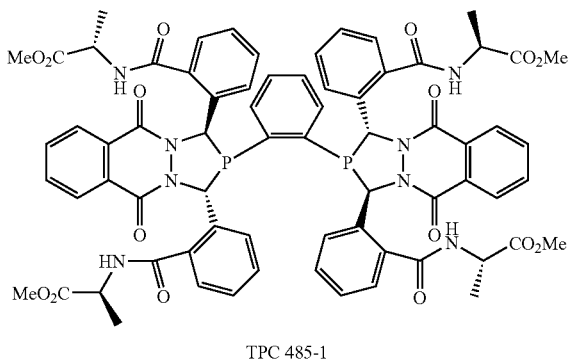

TPC 485-1

EXAMPLE 3

TPC485-1 (N,N',N'',N'''-(1,2-phenylenebis(((1R,3R)-5,10-dihydro-5,10-dioxo-1H-(1,2,4)diazaphospholo(1,2-b)phthalazine-2,1,3(3H)-triyl)bis(2,1-phenylenecarbonyl))) tetrakis-L-alanine-tetramethyl ester). Yield=21%. $^1$H NMR ($C_6D_6$): δ 1.30 (d, 6H, J=7.2 Hz, $CHCH_3$), 1.49 (d, 6H, J=7.3 Hz, $CHCH_3$), 3.39 (s, 6H, $CO_2CH_3$), 3.69 (s, 6H, $CO_2CH_3$), 4.68 (quintet, 2H, J=7.3 Hz, $CHCH_3$), 5.27 (quintet, 2H, J=7.3 Hz, $CHCH_3$), 6.5–7.2 (m, 14H), 7.52 (t, 2H, J=7.2 Hz), 7.63 (m, 4H), 7.78 (d, 2H, J=7.3 Hz), 7.9–8.1 (m, 10H), 8.85 (d, 2H, J=8.1 Hz, $NHCHCH_3$), 9.73 (d, 2H, J=8.1 Hz); $^{13}$C NMR ($C_6D_6$): δ 18.1 (s, $CHCH_3$), 18.8 (s, $CHCH_3$), 48.7 (s, $CHCH_3$), 48.9 (s, $CHCH_3$), 52.2 (s, $CO_2CH_3$), 52.8 (s, $CO_2CH_3$), 58.1 (broad, PCHN), 60.2 (t, $J_{C-P}$=16 Hz, PCHN), peaks at 125–140 have not been assigned, 156.8 (s, CONN), 157.3 (s, CONN), 169.0 (s, 2CONH), 174.1 (s, $CO_2CH_3$), 174.8 (s, $CO_2CH_3$); $^{31}$P NMR ($C_6D_6$): δ 4.5 (broad). EMM calcd for $C_{70}H_{64}N_8O_{16}P_2Na$ [M+Na]$^+$: 1357.381. found: 1357.382.

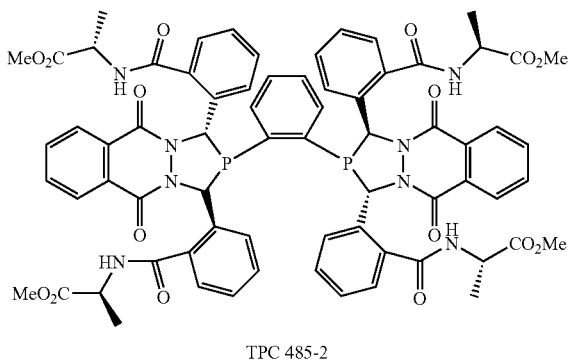

TPC 485-2

EXAMPLE 4

TPC485-2 (N,N',N'',N'''-(1,2-phenylenebis(((1S,3S)-5,10-dihydro-5,10-dioxo-1H-(1,2,4)diazaphospholo(1,2-b)phthalazine-2,1,3(3H)-triyl)bis(2,1-phenylenecarbonyl))) tetrakis-L-alanine-tetramethyl ester). Yield=21%. $^1$H NMR (($CD_3$)$_2$CO): δ 1.31 (d, 6H, J=7.3 Hz, $CHCH_3$), 1.53 (d, 6H, J=7.3 Hz, $CHCH_3$), 3.66 (s, 6H, $CO_2CH_3$), 3.74 (s, 6H, $CO_2CH_3$), 4.30 (broad, 2H, $CHCH_3$), 4.75 (quintet, 2H, J=7.4 Hz, $CHCH_3$), 6.34 (broad, 2H), 6.70 (broad, 2H), 6.84 (broad, 2H), 6.9–7.2 (m, 4H), 7.3–7.8 (m, 16H), 7.84 (m, 4H, phthaloyl), 8.05 (m, 2H, phthaloyl), 8.19 (m, 2H, phthaloyl), 9.26 (broad, 2H, $NHCHCH_3$); $^{13}$C NMR (($CD_3$)$_2$CO): δ 17.5 (s, $CHCH_3$), 18.1 (s, $CHCH_3$), 49.4 (s, $CHCH_3$), 49.6 (s, $CHCH_3$), 52.5 (s, $CO_2CH_3$), 52.6 (s, $CO_2CH_3$), 59.4 (s, PCHN), 62.1 (t, $J_{C-P}$=18 Hz, PCHN), peaks at 125–145 have not been assigned, 156.5 (s, CONN), 157.4 (s, CONN), 168.6 (s, CONH), 168.8 (s, CONH), 173.4 (s, $CO_2CH_3$), 173.7 (s, $CO_2CH_3$); $^{31}$P NMR (($CD_3$)$_2$CO): δ −7.6 (broad). EMM calcd for $C_{70}H_{64}N_8O_{16}P_2Na$ [M+Na]$^+$: 1357.381. found: 1357.376.

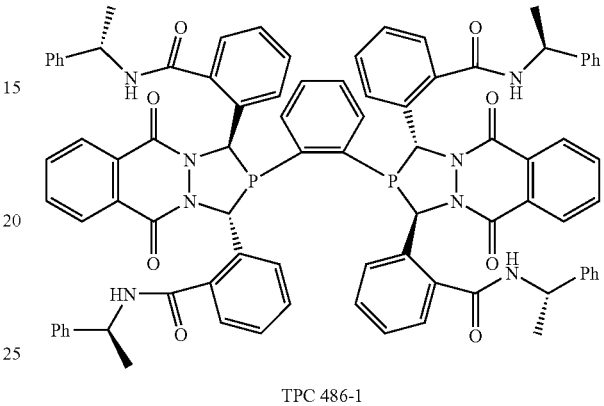

TPC 486-1

EXAMPLE 5

TPC486-1 (2,2',2'',2'''-(1,2-phenylenebis((1R,3R)-5,10-dihydro-5,10-dioxo-1H-(1,2,4)diazaphospholo(1,2-b)phthalazine-2,1,3(3H)-triyl))tetrakis(N-((1S)-1-phenylethyl)-benzamide). Yield=12%. $^1$H NMR (d-THF): δ 1.44 (d, 6H, J=6.3 Hz, $CH_3$), 1.65 (d, 6H, J=6.8 Hz, $CH_3$), 5.19 (broad quintet, 2H, J=7.1 Hz, $CHCH_3$), 5.49 (broad quintet, 2H, J=7.3 Hz, $CHCH_3$), 6.30 (d, 2H, J=7.5 Hz), 6.62 (t, 2H, J=7.0 Hz), 6.9–7.7 (m, 40H), 7.71 (m, 4H, phthaloyl), 7.93 (d, 2H, J=7.0 Hz, $NHCHCH_3$), 8.10 (m, 2H, phthaloyl), 8.21 (m, 2H, phthaloyl), 9.62 (d, 2H, J=7.3 Hz, $NHCHCH_3$); $^{13}$C NMR (d-THF): δ 22.7 (s, $CH_3$), 23.4 (s, $CH_3$), 49.8 (s, $CHCH_3$), 49.9 (s, $CHCH_3$), 59.4 (s, PCHN), 61.0 (d, $J_{C-P}$=16 Hz, PCHN), peaks at 125–150 ppm have not been assigned, 156.8 (s, CONN), 157.3 (s, CONN), 167.9 (s, CONH), 168.2 (s, CONH); $^{31}$P NMR (d-THF): δ −5.4 (broad). EMM calcd for $C_{86}H_{72}N_8O_8P_2Na$ [M+Na]$^+$: 1429.485. found: 1429.471.

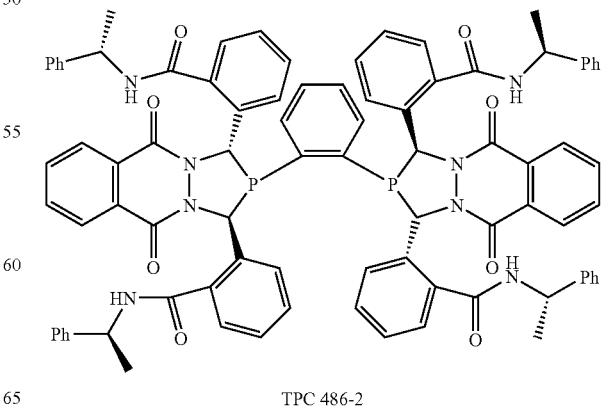

TPC 486-2

EXAMPLE 6

TPC486-2 (2,2',2'',2'''-(1,2-phenylenebis((1S,3S)-5,10-dihydro-5,10-dioxo-1H-(1,2,4)diazaphospholo(1,2-b)phthalazine-2,1,3(3H)-triyl))tetrakis(N-((1S)-1-phenylethyl)-benzamide). Yield=16%. $^1$H NMR (d-THF): δ 1.23 (d, 6H, J=7.0 Hz, CH$_3$), 1.61 (d, 6H, J=6.8 Hz, CH$_3$), 5.15 (m, 2H, NHCHCH$_3$), 5.46 (m, 2H, NHCHCH$_3$), 5.80 (d, 2H, J=7.8 Hz), 6.03 (t, 2H, J=7.4 Hz), 6.50 (s, 2H, PCHN), 6.76 (t, 2H, J=7.5 Hz), 7.0–8.0 (m, 42H), 8.07 (m, 2H), 8.25 (m, 2H), 9.70 (d, 2H, J=7.9 Hz, NHCHCH$_3$); $^{13}$C NMR (d-THF): δ 22.4 (s, CH$_3$), 23.8 (s, CH$_3$), 49.6 (s, CHCH$_3$), 50.7 (s, CHCH$_3$), 59.4 (broad s, PCHN), 62.5 (d, $J_{C-P}$=18 Hz, PCHN), peaks at 125–150 have not been assigned, 156.3 (s, CONN), 157.4 (s, CONN), 167.9 (s, CONH), 168.1 (s, CONH); $^{31}$P NMR (d-THF): δ –7.7 (broad). EMM calcd for C$_{86}$H$_{72}$N$_8$O$_8$P$_2$Na [M+Na]$^+$: 1429.485. found: 1429.475. Further characterization of TPC486-2, by X-ray crystallography, is described in Example 15.

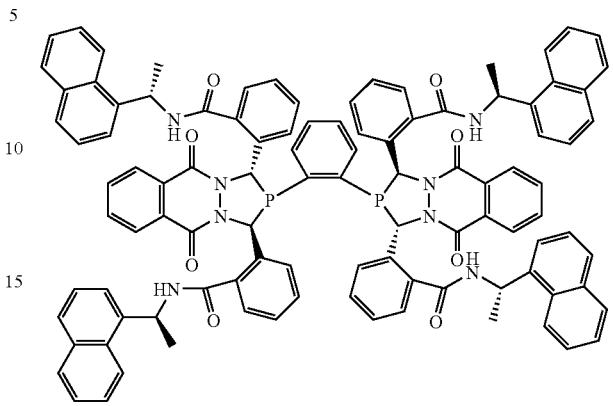

TPC 662-2

EXAMPLE 8

TPC662-2 (2,2',2'',2'''-(1,2-phenylenebis((1S,3S)-5,10-dihydro-5,10-dioxo-1H-(1,2,4)diazaphospholo(1,2-b)phthalazine-2,1,3(3H)-triyl))tetrakis(N-((1S)-1-(1-naphthalenyl)ethyl)-benzamide). Yield=30%. $^1$H NMR ((CD$_3$)$_2$O): (peaks were too broad to determine coupling constants) δ 1.30 (6H, CH$_3$), 1.64 (6H, CH$_3$), 5.71 (2H), 5.85 (2H), 5.98 (2H, CHCH$_3$), 6.15 (2H), 6.22 (2H, CHCH$_3$), 6.46 (s, 2H, PCHN), 7.0–8.5 (56H), 9.46 (2H, NHCHCH$_3$); $^{13}$C NMR ((CD$_3$)$_2$O): δ 21.3 (s, CH$_3$), 23.5 (s, CH$_3$), 45.7 (s, CHCH$_3$), 46.6 (s, CHCH$_3$), 60.2 (broad, PCHN), 62.4 (t, $J_{C-P}$=17.4 Hz, PCHN), peaks at 120–145 ppm have not been assigned, 156.3 (s, CONN), 157.2 (s, CONN), 168.4 (s, CONH), 168.6 (s, CONH); $^{31}$P NMR ((CD$_3$)$_2$O): δ –10.5 (broad). EMM calcd for C$_{102}$H$_{80}$N$_8$O$_8$P$_2$Na [M+Na]$^+$: 1629.547. found: 1629.540.

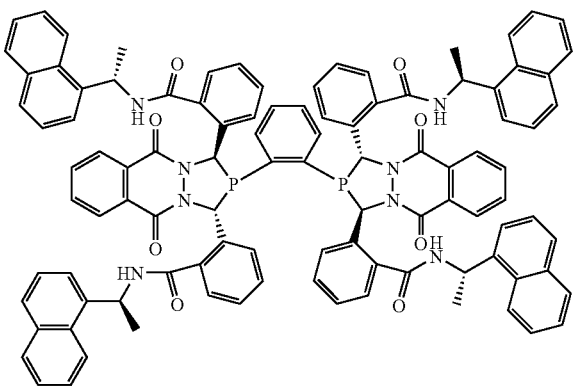

TPC 662-1

EXAMPLE 7

TPC662-1 (2,2',2'',2'''-(1,2-phenylenebis((1R,3R)-5,10-dihydro-5,10-dioxo-1H-(1,2,4)diazaphospholo(1,2-b)phthalazine-2,1,3(3H)-triyl))tetrakis(N-((1S)-1-(1-naphthalenyl)ethyl)-benzamide). Yield=33%. $^1$H NMR ((CD$_3$)$_2$O): (peaks were too broad to determine coupling constants) δ 1.60 (6H, CH$_3$), 1.77 (6H, CH$_3$), 5.95 (2H, CHCH$_3$), 6.27 (2H, CHCH$_3$), 6.42 (2H), 6.70 (2H), 6.9–8.6 (50H), 9.68 (2H, NHCHCH$_3$); $^{13}$C NMR ((CD$_3$)$_2$O): δ 22.9 (s, 2CH$_3$), 46.2 (s, CHCH$_3$), 46.5 (s, CHCH$_3$), 59.7 (broad, PCHN), 61.2 (t, $J_{C-P}$=15.9 Hz, PCHN), peaks at 120–145 ppm have not been assigned, 157.2 (s, CONN), 157.3 (s, CONN), 168.4 (s, CONH), 168.5 (s, CONH); $^{31}$P NMR ((CD$_3$)$_2$O): δ –4.1 (broad). EMM calcd for C$_{102}$H$_{80}$N$_8$O$_8$P$_2$Na [M+Na]$^+$: 1629.547. found: 1629.537.

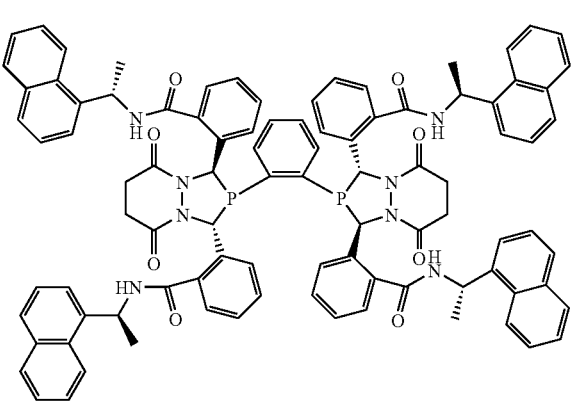

TPC 636-1

EXAMPLE 9

TPC636-1 (2,2',2",2'"-(1,2-phenylenebis((1R,3R)-tetrahydro-5,8-dioxo-1H-(1,2,4)diazaphospholo(1,2-a)pyridazine-2,1,3(3H)-triyl))tetrakis(N-((1S)-1-(1-naphthalenyl)ethyl)-benzamide). Yield=15%. $^1$H NMR ((CD$_3$)$_2$O): δ 1.59 (d, 6H, J=6.8 Hz, CH$_3$), 1.75 (d, 6H, J=6.8 Hz, CH$_3$), 2.3–3.0 (m, 8H, CH$_2$CH$_2$), 5.91 (dq, 2H, J=7.5, 6.8 Hz, CHCH$_3$), 6.26 (dq, 2H, J=7.1, 6.8 Hz, CHCH$_3$), 6.45 (d, 2H, J=7.6 Hz), 6.61 (s, 2H, PCHN), 6.67 (d, 2H, J=7.3 Hz), 6.80 (t, 2H, J=7.3 Hz), 6.88 (t, 2H, J=7.5 Hz), 7.02 (t, 2H, J=8.8 Hz), 7.1–7.9 (m, 34H), 7.95 (d, 2H, J=8.1 Hz), 8.10 (d, 2H, J=7.9 Hz), 8.40 (d, 2H, J=8.3 Hz, NHCHCH$_3$), 8.47 (d, 2H, J=8.3 Hz), 9.50 (d, 2H, J=8.3 Hz, NHCHCH$_3$); $^{13}$C{$^1$H} NMR ((CD$_3$)$_2$O): δ 22.8 (s, CH$_3$), 22.9 (s, CH$_3$), 46.1 (s, CH$_2$CH$_2$), 46.2 (s, CH$_2$CH$_2$), 56.6 (s, PCHN), 57.7 (d, J$_{C-P}$=13 Hz, PCHN), peaks at 120–140 ppm have not been assigned, 166.6 (s, CO), 168.4 (s, CO), 168.6 (s, CO), 168.7 (s, CO); $^{31}$P NMR ((CD$_3$)$_2$O): δ 11.8. EMM calcd for C$_{94}$H$_{80}$N$_8$O$_8$P$_2$Na [M+Na]$^+$: 1533.547. found: 1533.538.

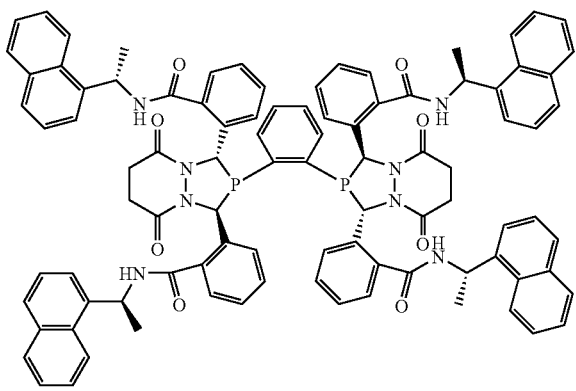

TPC 636-2

EXAMPLE 10

TPC636-2 (2,2',2",2'"-(1,2-phenylenebis((1S,3S)-tetrahydro-5,8-dioxo-1H-(1,2,4)diazaphospholo(1,2-a)pyridazine-2,1,3(3H)-triyl))tetrakis(N-((1S)-1-(1-naphthalenyl)ethyl)-benzamide). Yield=15%. $^1$H NMR (CD$_3$)$_2$O: δ 1.24 (d, 6H, J=7.5 Hz, CH$_3$), 1.66 (d, 6H, J=6.7 Hz, CH$_3$), 2.3–2.55 (m, 6H, CH$_2$CH$_2$), 2.75–2.95 (m, 2H, CH$_2$CH$_2$), 5.76 (t, 2H, J=7.6 Hz), 5.92 (dq, 2H, J=7.6, 7.2 Hz, CHCH$_3$), 5.98–6.10 (m, 6H), 6.20 (dq, 2H, J=7.5, 6.9 Hz, CHCH$_3$), 6.86 (d, 2H, J=7.2 Hz), 6.98 (m, 2H), 7.10 (m, 2H), 7.2–7.7 (m, 26H), 7.8–8.1 (m, 12H), 8.40 (d, 2H, J=8.3 Hz, NHCHCH$_3$), 9.31 (d, 2H, J=7.8 Hz, NHCHCH$_3$); $^{13}$C{$^1$H} NMR ((CD$_3$)$_2$O): δ 21.4 (s, CH$_3$), 23.3 (s, CH$_3$), 45.6 (s, CHCH$_3$), 46.7 (s, CHCH$_3$), 57.2 (t, J$_{C-P}$=6 Hz, PCHN), 59.4 (t, J$_{C-P}$=17 Hz, PCHN), peaks at 120–145 ppm have not been assigned, 166.5 (s, CO), 168.2 (s, 2CO), 168.6 (s, CO); $^{31}$P NMR ((CD$_3$)$_2$O): δ 4.2 (broad). EMM calcd for C$_{94}$H$_{80}$N$_8$O$_8$P$_2$Na [M+Na]$^+$: 1533.547. found: 1533.540.

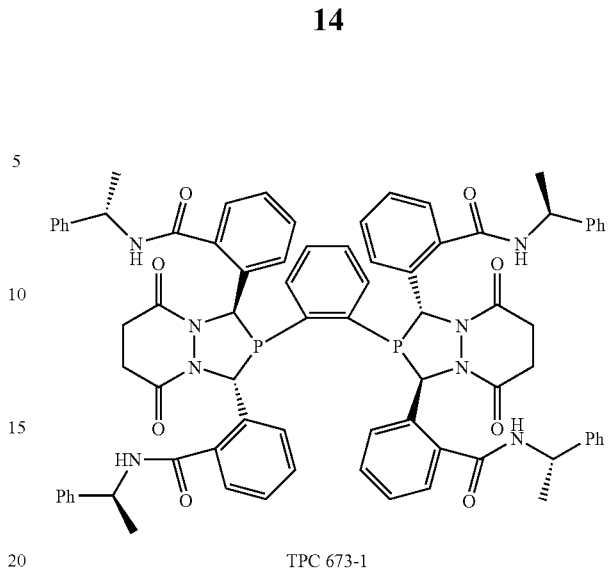

TPC 673-1

EXAMPLE 11

TPC673-1 (2,2',2",2'"-(1,2-phenylenebis((1R,3R)-tetrahydro-5,8-dioxo-1H-(1,2,4)diazaphospholo(1,2-a)pyridazine-2,1,3(3H)-triyl))tetrakis(N-((1S)-1-phenylethyl)-benzamide). Yield=21%. $^1$H NMR (d-THF): δ 1.37 (d, 6H, J=6.7 Hz, CH$_3$), 1.56 (d, 6H, J=6.7 Hz, CH$_3$), 2.2–2.7 (m, 6H, CH$_2$CH$_2$), 2.65–3.0 (m, 2H, CH$_2$CH$_2$), 5.06 (dq, 2H, J=7.5, 6.9 Hz, CHCH$_3$), 5.41 (dq, 2H, J=7.7, 6.9 Hz, CHCH$_3$), 6.39 (d, 2H, J=7.3 Hz), 6.5–6.9 (m, 10H), 7.06–7.36 (m, 26H), 7.51 (m, 2H), 7.60 (d, 4H, J=7.4 Hz), 7.97 (d, 2H, J=8.3 Hz, NHCHCH$_3$), 9.23 (d, 2H, J=7.8 Hz, NHCHCH$_3$); $^{13}$C NMR (d-THF): δ 23.2 (s, CH$_3$), 23.7 (s, CH$_3$), 29.6 (s, CH$_2$), 30.6 (s, CH$_2$), 50.0 (s, CHCH$_3$), 50.3 (s, CHCH$_3$), 56.9 (broad, PCHN), 57.6 (t (broad), PCHN), peaks at 125–150 ppm have not been assigned, 166.7 (s, CO), 168.2 (s, CO), 168.4 (s, CO), 168.5 (s, CO); $^{31}$P NMR (d-THF): δ 11.0 (broad). EMM calcd for C$_{78}$H$_{72}$N$_8$O$_8$P$_2$Na [M+Na]$^+$: 1333.485. found: 1333.480.

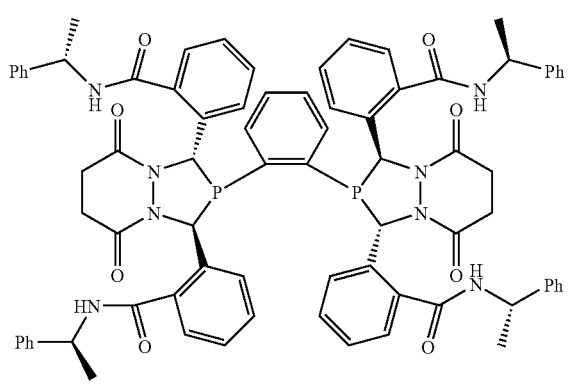

TPC 673-2

EXAMPLE 12

TPC673-2 (2,2',2'',2'''-(1,2-phenylenebis((1S,3S)-tetrahydro-5,8-dioxo-1H-(1,2,4)diazaphospholo(1,2-a)pyridazine-2,1,3(3H)-triyl))tetrakis(N-((1S)-1-phenylethyl)-benzamide). Yield=16%. $^1$H NMR (d-THF): δ 1.14 (d, 6H, J=7.1 Hz, CH$_3$), 1.56 (d, 6H, J=7.1 Hz, CH$_3$), 2.3–2.9 (m, 8H, CH$_2$CH$_2$), 5.04 (dq, 2H, J=8.0, 7.1 Hz, CHCH$_3$), 5.39 (dq, 2H, J=7.2, 7.0 Hz, CHCH$_3$), 6.0–6.2 (m, 6H), 6.61 (t, 2H, J=7.5 Hz), 6.8–7.3 (m, 30H), 7.36 (d, 2H, J=8.0 Hz, NHCHCH$_3$), 7.5–7.7 (m, 6H), 9.28 (d, 2H, J=7.6 Hz, NHCHCH$_3$); $^{13}$C{$^1$H} NMR (d-THF): δ 22.4 (s, CH$_3$), 23.6 (s, CH$_3$), 30.0 (s, CH$_2$), 30.2 (s, CH$_2$), 49.7 (s, CHCH$_3$), 50.8 (s, CHCH$_3$), 56.8 (s, PCHN), 59.4 (t, J$_{C-P}$=17 Hz, PCHN), peaks at 125–150 have not been assigned, 166.8 (s, CO), 168.1 (s, CO), 168.2 (s, 2CO); $^{31}$P NMR (d-THF): δ 5.8 (broad). EMM calcd for C$_{78}$H$_{72}$N$_8$O$_8$P$_2$Na [M+Na]$^+$: 1333.485. found: 1333.480.

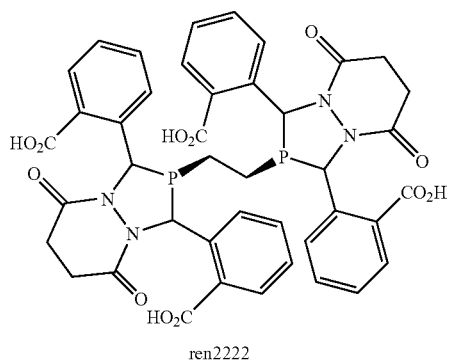

ren2222

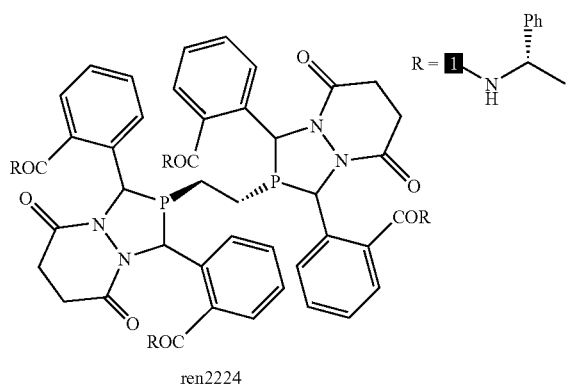

ren2224

EXAMPLE 13

Syntheses of Bis(3,4-Diazaphosphino)ethane (RCN2224) via tetra carboxylic acid intermediate (RCN2222)

Bisphosphinoethane (0.21 mL, 2.25 mmol, 1 equiv) and succinyl chloride (0.76 mL, 6.7 mmol, 3 equiv), respectively, were added to a THF (35 mL) solution of 2,2'-(azinodimethylidyne)bis-benzoic acid (1.334 g, 4.5 mmol, 2 equiv), which resulted in a brown solution and an almost immediate precipitation of solid. After stirring for 16 h, the supernatant was filtered away from the solid. The solid was washed with THF (2×30 mL) and dried under vacuum to yield the bis(benzoic acid diazaphospholano)ethane, RCN2222, as an off-white solid (1:1 mixture of 2 diastereoisomers, 1.28 g, 1.39 mmol, 62% yield), which was used directly without further purification. A sample of RCN2222 (253 mg, 0.275 mmol, 1 equiv) and PyBOP (benzotriazol-1-yl-oxy-tris-pyrrolidino-phosphonium hexafluorophosphate; 647 mg, 1.24 mmol, 4.5 equiv) were suspended in CH$_2$Cl$_2$ (30 mL). After respective addition of diisopropylethylamine (0.23 mL, 1.32 mmol, 4.8 equiv) and (S)-methylbenzylamine (0.2 mL, 1.55 mmol, 5.6 equiv), an immediate dissolution of all the reaction components occurred. After stirring for 16 h, the solution was diluted with CH$_2$Cl$_2$ (50 mL) and extracted with 3 M HCl (75 mL), saturated NaHCO$_3$ (75 mL), and H$_2$O (75 mL). The organic layer was dried with MgSO$_4$ and the solvent was removed under vacuum. The crude product was purified by column chromatography (gradient of 4:1 EtOAc:Hexanes to 12:3:2 EtOAc:Hexanes:MeOH), yielding a small amount of one diastereoisomer of RCN2224 as a white solid (23 mg, 1.7×10$^{-2}$ mmol, 6% yield) and several fractions consisting of various mixtures of diastereoisomers and PyBOP oxide. $^1$H NMR (CDCl$_3$) for RCN2224: δ6.8–7.5(multiplet, 36H), δ6.3(s, 2H, CH), δ6.2(s, 2H, CH), δ5.1(septet, 4H, CH), δ3.0(multiplet, 2H), δ2.6(multiplet, 6H), δ1.5 (d, 6H, CH$_3$), δ1.3(d, 6H, CH$_3$), δ0.9(broad, 2H), δ0.7(broad, 2H).

EXAMPLE 14

TPC-300 and TPC-356

These ligands, as depicted below, were synthesized according to literature procedure (Clark, T. P.; Landis, C. R. J. Am. Chem. Soc. 2003, 125, 11792.)

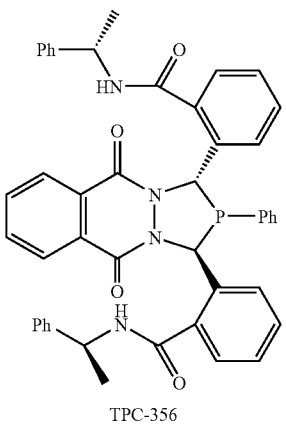

TPC-356

2,2'-[(1S,3S)-2,3,5,10-tetrahydro-5,10-dioxo-2-phenyl-1H-[1,2,4]diazaphospholo[1,2-b]phthalazine-1,3-diyl]bis[N-[(1S)-1-phenylethyl]-benzamide

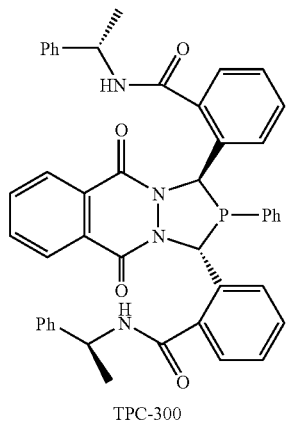

TPC-300

2,2'-[(1R,3R)-2,3,5,10-tetrahydro-5,10-dioxo-2-phenyl-1H-[1,2,4]diazaphospholo[1,2-b]phthalazine-1,3-diyl]bis[N-[(1S)-1-phenylethyl]-benzamide

EXAMPLE 15

Asymmetric Hydroformylation Procedures

Hydroformylation solutions were prepared by addition of ligand and Rh(CO)$_2$(acac) stock solutions to toluene followed by addition of solvent and then olefin solution. Total volume of solution in each reactor cell was 4.5 mL. Ligand solutions (0.03 M for bidentate ligands and 0.06 M for monodentate ligands in THF) and Rh(CO)$_2$(acac) (0.05 M in toluene) were prepared in the dry box at room temperature. The allyl cyanide solution was prepared by mixing 15.32 g of allyl cyanide, 3.25 g of decane (as a GC internal standard) and 6.31 g of toluene (1:0.1:0.3 molar ratio). The styrene solution was prepared by mixing 14.22 g of styene and 6.98 g of dodecane (1:0.3 molar ratio). The vinyl acetate solution was prepared by mixing 13.43 g of vinyl acetate and 7.97 g of dodecane (1:0.3 molar ratio). The styene/allyl cyanide/vinyl acetate/dodecane solution was prepared by mixing 11.71 g of styene, 7.54 g of allyl cyanide, 9.68 g of vinyl acetate and 5.75 g of dodecane (1:1:1:0.3 molar ratio).

Hydroformylation reactions were conducted in an Argonaut Endeavor® reactor system housed in an inert atmosphere glove box. The reactor system consists of eight parallel, mechanically stirred pressure reactors with individual temperature and pressure controls. Upon charging the catalyst solutions, the reactors were pressurized with desired pressure of syn gas (H$_2$:CO 1:1) and then heated to the desired temperature while stirring at 800 rpm. The runs were stopped after 3 hrs by venting and cooling the system. Upon opening the reactor 50 μL of each reaction mixture was taken out and diluted with 1.6 mL of toluene, and this solution was analyzed by gas chromatography. For analysis of styrene and vinyl acetate products Supelco's Beta Dex 225 column was used. Temperature program of 100° C. for 5 min, then 4° C./min to 160° C.; retention times: 2.40 min for vinyl acetate, 6.76 (S) and 8.56 (R) min for the enantiomers of the acetic acid 1-methyl-2-oxo-ethyl ester (branched regioisomer), 11.50 min for acetic acid 3-oxo-propyl ester (linear regioisomer), 12.11 (S) and 12.34 (R) min for the enantiomers of 2-phenyl-propionaldehyde (branched regioisomer) and 16.08 min for 3-phenyl-propionaldehyde (linear regioisomer). For allyl cyanide product analysis Astec Chiraldex A-TA column was used. Temperature program of 90° C. for 7 min, then 5° C./min to 180° C.; retention times: 5.55 min for allyl cyanide, 14.79 (S) and 15.28 (R) min for the enantiomers of the 3-methyl-4-oxo-butyronitrile (branched regioisomer), and 19.46 min for 5-oxo-pentanenitrile (linear regioisomer). Results of hydroformylation reactions are summarized in Table 1 and Table 2.

TABLE 1

Asymmetric hydroformylation of styrene (St), allyl cyanide (AC) and vinyl acetate (VA).

| Entry | Ligand | Conversion (%)[a] (St, AC, VA) | Regioselectivity (b/l[b]) (St, AC, VA) | Enantioselectivity (% ee, configuration) (St, AC, VA) |
|---|---|---|---|---|
| 1 | TPC-485-1 | 78, 99, 84 | 6.7, 5.0, 26.3 | 70 (S), 61 (R), 84 (R) |
| 2 | TPC-485-2 | 54, 97, 57 | 9.7, 5.7, 19.5 | 75 (R), 61 (S), 79 (S) |
| 3 | TPC-673-1 | 100, 100, 100 | 6.3, 4.1, 30.7 | 73 (R), 77 (S), 91 (S) |
| 4 | TPC-673-2 | 100, 100, 100 | 6.8, 4.0, 36.1 | 79 (S), 84 (R), 96 (R) |
| 5 | TPC-486-1 | 95, 100, 96 | 8.2, 5.3, 23.6 | 75 (R), 63 (S), 84 (S) |
| 6 | TPC-486-2 | 100, 100, 100 | 8.2, 4.2, 23.7 | 75 (S), 74 (R), 92 (R) |
| 7 | TPC-662-1 | 98, 100, 99 | 8.6, 5.6, 22.4 | 75 (R), 67 (S), 83 (S) |
| 8 | TPC-662-2 | 100, 100, 100 | 7.4, 3.8, 20.6 | 63 (S), 73 (R), 91.4 (R) |
| 9 | TPC-636-1 | 100, 100, 100 | 5.4, 4.0, 35.8 | 64 (R), 68.5 (S), 86 (S) |
| 10 | TPC-636-2 | 99, 100, 100 | 5.2, 3.5, 41.1 | 73 (S), 81 (R), 96 (R) |
| 11 | RCN2224 | 100, 100, 100 | 7.1, 6.1, 58.0 | 64 (R), 67 (S), 72 (S) |
| 12 | TPC-300 | 31, 92, 36 | 1.1, 1.3, 39.8 | 12 (S), 10 (R), 23 (R) |
| 13 | TPC-356 | 28, 93, 30 | 1.1, 1.4, 35.9 | 8 (R), 13.7 (S), 23 (S) |
| 14 | (2R,4R)-Chiraphite | 91, 100, 75 | 9.2, 5.5, 177 | 46 (S), 13 (R), 50 (S) |
| 15 | (S,S)-Kelliphite | 79, 100, 79 | 8.9, 9.3, 61.0 | 2 (S), 66 (S), 73 (S) |
| 16 | (R,S)-Binapbos[c] | 96, 95, 55 | 5.3, 2.1, 6.2 | 85 (R), 73 (S), 59 (S) |

Pressure = 150 psi (1:1 H$_2$/CO), Ligand:Rh = 1.2:1 for bidentate and 2.4:1 for monodentate phosphites, solvent = toluene, temp = 80° C. Solution volume—4.5 mL. Olefins:Rh = 5000:1. [a]Percentage conversion of olefins after 3 hrs. [b]b/l = branched to linear ratio. Each data point is an average obtained from two independent runs. [c]Olefin:Rh = 2000:1

TABLE 2

Asymmetric hydroformylation of styrene (St), allyl cyanide (AC) and vinyl acetate (VA) with TPC-673-2

| Entry | Temp. | Pressure | Conversion (%)[a] (St, AC, VA) | Regioselectivity (b/l[b]) (St, AC, VA) | Enantioselectivity (% ee, configuration) (St, AC, VA) |
|---|---|---|---|---|---|
| 1 | 40[c] | 150 | 21, 69, 29 | 26.4, 5.1, 48.8 | 87 (S), 66 (R), 96 (R) |
| 2 | 60[c] | 150 | 74, 100, 96 | 16.0, 4.8, 44.0 | 86 (S), 90 (R), 97 (R) |
| 3 | 80[c] | 150 | 100, 100, 100 | 7.5, 4.2, 37.5 | 80 (S), 85 (R), 96 (R) |
| 4 | 100[c] | 150 | 100, 100, 100 | 3.0, 3.7, 48.3 | 61 (S), 71 (R), 95 (R) |
| 5 | 80 | 20[d] | 7, 73, 33 | 1.5, 3.1, 37.7 | 36 (S), 84 (R), 95 (R) |
| 6 | 80 | 100[d] | 91, 100, 100 | 5.0, 3.9, 35.8 | 76 (S), 85 (R), 97 (R) |
| 7 | 80 | 200[d] | 93, 100, 99 | 8.7, 4.1, 36.5 | 82 (S), 85 (R), 96 (R) |
| 8 | 80 | 300[d] | 91.3, 100, 99 | 11.9, 4.1, 38.3 | 83 (S), 85 (R), 96 (R) |
| 9 | 80 | 400[d] | 92, 100, 98 | 14.5, 4.2, 37.4 | 84 (S), 85 (R), 96 (R) |
| 10 | 80 | 500[d] | 90, 100, 96 | 17.2, 4.2, 35.8 | 87 (S), 86 (R), 96 (R) |

Pressure = 150 psi (1:1 H/CO), Ligand:Rh = 1.2:1 for bidentate and 2.4:1 for monodentate phosphites, solvent = toluene, temp = 80° C. Solution volume—4.5 mL. [a]Percentage conversion of olefins after 3 hrs. [b]b/l = branched to linear ratio. Each data point is an average obtained from two independent runs. [c]Olefins:Rh = 2500:1, [d]Olefins:Rh = 10000:1

EXAMPLE 16

X-Ray Structure of TPC486-2

A crystal of the ligand TPC486-2 (prepared according to Example 6) was studied on a Bruker SMART PLATFORM diffractometer equipped with a graphite monochromatic crystal, a MoKα radiation source (λ=0.71073 Å), a CCD (charge coupled device) area detector. The crystal was bathed in a cold nitrogen stream for the duration of data collection (−100° C.). The space group was determined to be P21 (# 4) based on systematic absences. The structure was solved and refined in SHELXTL6.1 (Sheldrick, G. M. (2000), SHELXTL6.1. Crystallographic software package. Bruker AXS, Inc. Madison, Wis., USA). The asymmetric unit consists of the molecule and two THF molecules of crystallization. The latter molecules were disordered and could not be modeled properly, thus program SQUEEZE (P. van der Sluis & A. L. Spek (1990), SQUEEZE, Acta Cryst. A46, 194–201), a part of the PLATON (Spek, A. L. (1990). PLATON, Acta Cryst. A46, C-34) package of crystallographic software, was used to calculate the solvent disorder area and remove its contribution to the overall intensity data. The molecules have two disorders that were resolved and several that were not resolved. Phenyl ring between P1 and C51 (C2–16) is refined in two parts with their site occupation factors dependently refined. The terminal phenyl ring on C61 is also disordered and was refined in two parts; along with the methyl group on C61. It was refined in two parts with their site occupation factors also dependently refined. The previous disorder seems to induce an in-plane motion in the rest of the ligand which is most observed in the external aromatic ring C4–9. A similar motion is observed in ring C26–31. Disorders are also observed in all four terminal phenyl rings but only the one on C61 is large enough to allow its resolution. The central phenyl ring C45–50 is also slightly disordered due to a rotational motion around an axis passing through bond C45–C50. This motion can be seen in the large out of plane thermal ellipsoids. In the final cycle of refinement, 7896 observed reflections with I>2σ(I) were used to refine 898 parameters and the resulting $R_1$, $wR_2$ and S (goodness of fit) were 5.69%, 11.63% and 0.803, respectively. A space group $P2_1$ is a chiral indicating the absence of any inversion or reflection crystallographic symmetry. Consequently, only one enantiomer exists in the data crystal and that is deduced from the value of the Flack x parameter which refined to 0.01(8). A value of zero indicates that the correct enantiomer was used for the successful refinement of the structure.

The invention claimed is:

1. A process for subjecting an olefin to an asymmetric reaction selected from the group consisting of hydroformylation, hydrocyanation, hydrocarboxylation and hydroesterification, which is carried out in the presence of, as catalyst, a transition metal complex of a bis(diazaphospholane) ligand according to formula (1), or the opposite enantiomer thereof, wherein (a) Bridge is a linking group selected from the group consisting of substituted and unsubstituted alkyl, substituted and unsubstituted alkenyl, substituted and unsubstituted aryl, substituted and unsubstituted heterocyclyl, and substituted and unsubstituted ferrocenyl groups; (b) W, at each occurrence, is independently selected from the group consisting of substituted and unsubstituted aryl and heteroaryl, substituted and unsubstituted cycloalkyl, substituted and unsubstituted heterocyclyl, and substituted and unsubstituted alkyl; (c) T, at each occurrence, is independently selected from the group consisting of —C(O)OR$^3$, —C(O)NR$^4$R$^5$, —C(O)N(R$^4$)OR$^5$, OR$^3$, NR$^4$R$^5$, substituted and unsubstituted oxazole, substituted and unsubstituted oxazoline, substituted and unsubstituted oxazolidine, and substituted and unsubstituted alkyl; (d) R$^1$ and R$^2$ are independently selected from the group consisting of H, substituted and unsubstituted alkyl, substituted and unsubstituted cycloalkyl, and substituted and unsubstituted aryl; or R$^1$ and R$^2$ may join together to form a substituted or unsubstituted aryl, a substituted or unsubstituted cycloalkyl, or a substituted or unsubstituted cycloalkenyl; (e) R$^3$, R$^4$ and R$^5$ are each independently selected from the group consisting of —H, substituted and unsubstituted alkyl, substituted and unsubstituted aryl, substituted and unsubstituted aralkyl, substituted and unsubstituted heterocyclyl, substituted and unsubstituted heterocyclylalkyl; or R$^4$ and R$^5$ may join together to form a non-aromatic heterocyclyl; and (f) the dashed line, at each occurrence, represents an optional additional bond, such that a single or double carbon-carbon bond exists between C(R$^1$) and C(R$^2$)

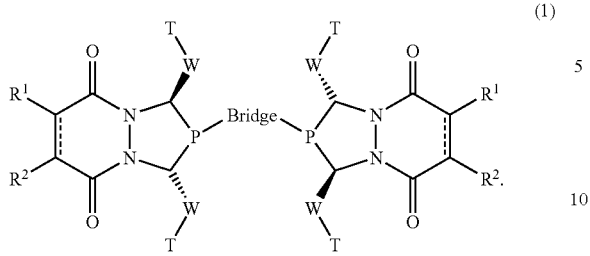
(1)

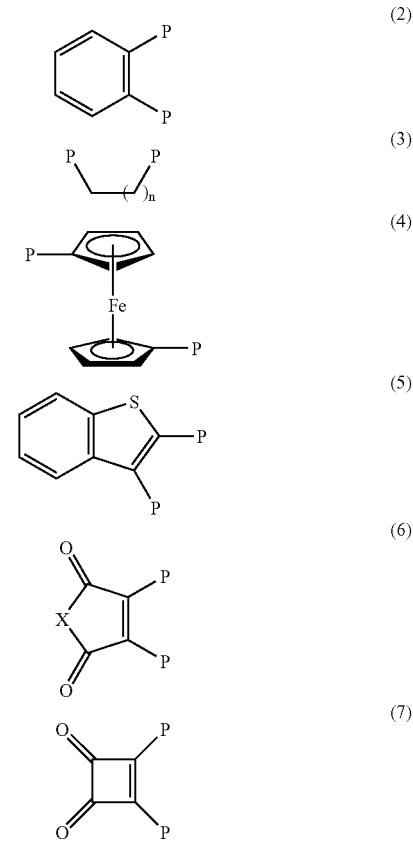

2. A process according to claim 1, wherein the transition metal is selected from the group consisting of rhodium, ruthenium, iridium, palladium, cobalt, platinum, nickel, iron and osmium.

3. A process according to claim 2, wherein the transition metal is rhodium.

4. A process according to claim 1, where the asymmetric reaction is either hydroformylation or hydrocyanation.

5. A process according to claim 4, wherein the reaction is asymmetric hydroformylation of an olefin and the complex is a rhodium complex.

6. A process according to claim 5, comprising enantioselective hydroformylation of a prochiral olefin.

7. A process according to claim 5, comprising diastereoselective hydroformylation of an enantiomerically enriched chiral olefin.

8. A process according to claim 6, wherein the olefin is an α-olefin.

9. A process according to claim 8, wherein the branched aldehyde produced in the reaction has an enantiomeric excess (ee) of at least 60%.

10. A process according to claim 9, wherein the branched aldehyde has an ee of at least 80%.

11. A process according to claim 8, wherein the ratio of branched:linear aldehyde products is at least 3:1.

12. A process according to claim 9, wherein the ratio of branched:linear aldehyde products is at least 8:1.

13. A process according to claim 8, wherein the α-olefin is selected from the group consisting of styrene, vinyl acetate, and allyl cyanide.

14. A process according to claim 5, which further comprising derivatizing the aldehyde product.

15. A process according to claim 14, wherein the derivatizing reaction comprises an oxidation, reduction, amination, olefination, condensation, esterification, alkylation, arylation or acylation reaction.

16. A process according to claim 1, wherein the complex is either pre-formed and isolated prior to use, pre-formed in a solution that is then combined in the reaction vessel with the substrate undergoing reaction, or generated in situ during the reaction.

17. A process according the claim 16, wherein the complex is pre-formed in a solution that is then combined in the reaction vessel with the substrate undergoing reaction.

18. A process according to claim 1, wherein P-Bridge-P in compound (1) is selected from the group comprising formulae (2) to (7), each of which may be optionally substituted; n in (3) is in the range 0–5; X in (6) is either O or N-alkyl 19. A process according to claim 18, wherein P-Bridge-P is of formula (2).

20. A process according to claim 18, wherein P-Bridge-P is of formula (3) and n is 1.

21. A process according to claim 1, wherein every W-T group in compound (1) is identical.

22. A process according to claim 21, wherein W in compound (1) is either substituted or unsubstituted aryl or heteroaryl.

23. A process according to claim 22, wherein each T in W is ortho relative to the position attached to the diazaphospholane ring.

24. A process according to claim 23, wherein W is 1,2-phenylene.

25. A process according to claim 21, wherein T in compound (1) is —C(O)NR$^4$R$^5$.

26. A process according to claim 21, wherein NR$^4$R$^5$ is derived from a chiral amine H—NR$^4$R$^5$.

27. A process according to claim 26, wherein R$^4$ is H.

28. A process according to claim 26, whereon the chiral amine is either a 1-aryl ethylamine or an alkyl ester of an α-amino acid.

29. A process according to claim 28, wherein the chiral amine is selected from the group consisting of (R)-1-phenylethylamine, (S)-1-phenylethylamine, (R)-1-(1-naphthylethylamine), (S)-1-(1-naphthylethylamine), methyl and ethyl esters of (S)-alanine, methyl and ethyl esters of (R)-alanine.

30. A process according to claim 1, wherein each diazaphospholane ring in compound (1) is incorporated into a tricycle represented by partial formula (8)

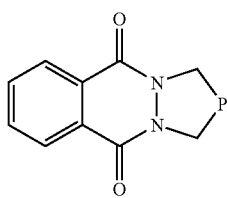
(8)
31. A process according to claim 1 wherein each diazaphospholane ring in compound (1) is incorporated into a bicycle represented by partial formula (9)
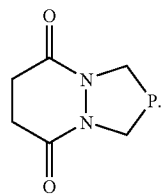
(9)
32. A process according to claim 30 or claim 31, wherein compound (1) is more specifically represented by formula (10), or the opposite enantiomer thereof
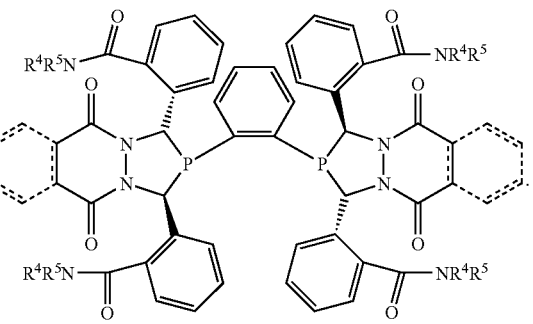
(10)
* * * * *